US007956350B2

(12) United States Patent
Inbasekaran et al.

(10) Patent No.: US 7,956,350 B2
(45) Date of Patent: Jun. 7, 2011

(54) CROSSLINKABLE SUBSTITUTED FLUORENE COMPOUNDS

(75) Inventors: Michael Inbasekaran, Palatine, IL (US); Wanglin Yu, Midland, MI (US)

(73) Assignee: Sumitomo Chemical Company, Limited, Tokyo (JP)

( * ) Notice: Subject to any disclaimer, the term of this patent is extended or adjusted under 35 U.S.C. 154(b) by 950 days.

(21) Appl. No.: 10/579,498

(22) PCT Filed: Oct. 25, 2004

(86) PCT No.: PCT/US2004/036075
§ 371 (c)(1),
(2), (4) Date: Aug. 14, 2006

(87) PCT Pub. No.: WO2005/049548
PCT Pub. Date: Jun. 2, 2005

(65) Prior Publication Data
US 2007/0063191 A1 Mar. 22, 2007

Related U.S. Application Data

(60) Provisional application No. 60/520,597, filed on Nov. 17, 2003.

(51) Int. Cl.
*H01L 51/30* (2006.01)
*H01L 51/54* (2006.01)
*C08G 61/00* (2006.01)

(52) U.S. Cl. .......... 257/40; 528/422; 528/423; 428/917; 313/504; 313/506; 257/E51

(58) Field of Classification Search .................. 428/690, 428/917; 257/40, E51; 528/422, 423; 313/504, 313/506
See application file for complete search history.

(56) References Cited

U.S. PATENT DOCUMENTS

| 4,983,482 | A |  | 1/1991 | Ong et al. |
| 5,034,296 | A | * | 7/1991 | Ong et al. .............. 430/58.7 |
| 5,378,519 | A | * | 1/1995 | Kikuchi et al. .......... 428/690 |
| 5,728,801 | A |  | 3/1998 | Wu et al. |
| 5,777,070 | A |  | 7/1998 | Inbasekaran et al. |
| 5,929,194 | A |  | 7/1999 | Woo et al. |
| 5,962,631 | A |  | 10/1999 | Woo et al. |
| 6,169,163 | B1 |  | 1/2001 | Woo et al. |
| 6,255,447 | B1 |  | 7/2001 | Woo et al. |
| 6,255,449 | B1 |  | 7/2001 | Woo et al. |
| 6,362,310 | B1 |  | 3/2002 | Woo et al. |
| 6,605,373 | B2 |  | 8/2003 | Inbasekaran et al. |
| 7,012,123 | B2 | * | 3/2006 | Ishizawa et al. ......... 526/284 |
| 2003/0124382 | A1 | * | 7/2003 | Taguchi et al. .......... 428/690 |
| 2003/0204036 | A1 |  | 10/2003 | Ishizawa et al. |
| 2003/0207153 | A1 |  | 11/2003 | Senoo et al. |
| 2003/0225234 | A1 | * | 12/2003 | Jaycox et al. .......... 526/329.7 |
| 2005/0239636 | A1 | * | 10/2005 | Gao et al. .............. 502/103 |

FOREIGN PATENT DOCUMENTS

| EP | 0 823 669 A1 | 2/1998 |
| EP | 0 875 947 A2 | 11/1998 |
| JP | 5-302081 A | 11/1993 |
| JP | 7-199503 | 8/1995 |
| JP | 08283708 A | 10/1996 |
| JP | 9-258465 | 10/1997 |
| JP | 11-322679 | 11/1999 |
| JP | 2000-16973 A | 1/2000 |
| JP | 2000-327640 | 11/2000 |
| JP | 2003-82035 A | 3/2003 |

OTHER PUBLICATIONS

Database CA Online!, Chemical Abstracts Service, Columbus, Ohio, US; 1995, Mashita, Kyokazu et al., "Electrophotographic imaging method", XP002312483 retrieved from STN Database accession No. 1995:921945 (corresponds to JP 07-199503 A Fuji Xerox Co., Ltd. Aug. 4, 1995, pp. 17-20.

Database CA Online!, Chemical Abstracts Service, Columbus, Ohio, US; 1997, Kikuchi, Norihiro et al: "Manufacture of charge-transporting compound and electrophotographic photoreceptor containing it", XP002312484 retrieved from STN Database accession No. 1997:648772 cited in the application abstract (corresponds to JP 09-258465 A Canon K. K., Japan, Oct. 3, 1997.

Hreha R.D. et al., "Synthesis of acrylate and norbornene polymers with pendent 2,7-bis(diarylamino) fluorine hole-transport groups", Tetrahedron, Elsevier Science Publishers, Amsterdam, NL, vol. 60, No. 34, Aug. 16, 2004, XP004547465, pp. 7169-7176.

Thomas Braig et al., "Crosslinkable hole-transporting polymers by palladium-catalyzed C-N-coupling reaction", Macromol. Rapid Commun., 2000, pp. 583-589, vol. 21, No. 9, Wiley-VCH Verlag GmbH, D-69451 Weinheim.

Kevin D. Belfield et al., "A new blue light-emitting oligofluorene glass: synthesis characterization and photophysical properties", Journal of Physical Organic Chemistry, 2003, pp. 194-201, vol. 16, Wiley Interscience.

Kevin D. Belfield et al., "Synthesis and Characterization of a Two-Photon Absorbing and Luminiscent Aminofluorenyl Polymer", Polymer Preprints, 2002, pp. 104-105, vol. 43., No. 1.

Kevin D. Belfield et al., "Two-Photon Absortion in a New Symmetrical Series of Dyphenylaminofluorene-Based Structures", Polymer Preprints, 2003, pp. 1061-1062, vol. 44., No. 1.

P.E. Burrows et al., "Metal ion dependent luminescence effects in metal tris-quinolate organic heterjunction light emitting devices", Applied Physics Letters, 1994, pp. 2718-2720, vol. 64, No. 20, American Institute of Physics.

Yuji Hamada et al., "High Luminance in Organic Electroluminescent Devices with Bis(10- hydroxybenzo[h]quinolinato)beryllium as an Emitter", Chemistry Letters, 1993, pp. 905-906, The Chemical Society of Japan.

(Continued)

*Primary Examiner* — D. Lawrence Tarazano
*Assistant Examiner* — J. L. Yang
(74) *Attorney, Agent, or Firm* — Sughrue Mion, PLLC

(57) ABSTRACT

Novel 2,7-di(arylamino)-substituted fluorenes that are further substituted at the 9-position with one or more crosslinkable moieties, oligomers or polymers formed by crosslinking of said crosslinkable moieties, methods for their preparation, and use thereof in forming solvent resistant films having use as interlayers in electronic devices, especially electroluminescent devices.

14 Claims, No Drawings

OTHER PUBLICATIONS

Yuji Hamada et al., "Organic Electroluminescent Devices with Bright Blue Emission", Optoelectronics-Devices and Technologies, 1992, pp. 83-93, vol. 7, No. 1, MITA Press.

Junji Kido et al., "Blue Electroluminescent 1,2,4-Triazole Derivative", Chemistry Letters, 1996, pp. 47-48.

Masayoshi Yoshida et al., "Three-layered multicolor organic electroluminescent device", Applied Physics Letters, 1996, pp. 734-736, vol. 69, No. 6, American Institute of Physics.

Xiao-Chang Li et al., "Synthesis and Optoelectronic Properties of Aromatic Oxadiazole Polymers", Journal of Chemical Society, Chemical Commun., 1995, pp. 2211-2212.

Y. Yang et al., "Electron injection polymer for polymer light-emitting diodes", Journal of Applied Physics, 1995, pp. 4807-4809, vol. 77, No. 9, American Institute of Physics.

Marko Strukelj et al., "Design and Application of Electron-Transporting Organic Materials", Science, 1995, pp. 1969-1972, vol. 267.

Takakazu Yamamoto et al., "Polymer Light-Emitting Diodes with Single- and Double-Layer Structures Using Poly(2,3-diphenylquinoxaline-5,8-diyl)", Japan Journal of Applied Physics, 1994, pp. L250-L253, vol. 33, Part 2, No. 2B.

D. O'Brien et al., "Electroluminescence applications of a poly(phenyl quinoxaline)", Synthetic Metals, 1996, pp. 105-108, vol. 76, Elsevier Science S.A.

M.S. Weaver et al., "Recent progress in polymers for electroluminescence: microcavity devices and electron transport polymers", Thin Solid Films, 1996, pp. 39-47, vol. 273, Elsevier Science S.A.

Masahiko Fukuda et al., "Fusible Conducting Poly(9-alkylfluorene) and Poly(9,9-dialkylfluorene) and Their Characteristics", Japanese Journal of Applied Physics, 1989, pp. L1433-L1435, vol. 28, No. 8.

Michael S. Bayer et al., "Crosslinkable hole-transport materials for preparation of multilayer organic light emitting devices by spin-coating", Macromol. Rapid Commun., 1999, pp. 224-228, vol. 20, No. 4, Wiley-VCH Verlag GmbH, D-69451 Weinheim.

Japanese Office Action corresponding to Japanese Patent Application No. 2006-539569 issued Oct. 5, 2010.

* cited by examiner

CROSSLINKABLE SUBSTITUTED FLUORENE COMPOUNDS

CROSS-REFERENCE STATEMENT

This application claims the benefit of U.S. Provisional Application No. 60/520,597, filed Nov. 17, 2003.

BACKGROUND OF THE INVENTION

This invention relates to novel 2,7-di(arylamino)fluorenes which are further substituted at the 9-position with one or more crosslinkable moieties and methods for the preparation of such compounds. The invention further relates to oligomers and polymers of such substituted fluorene compounds as well as films and coatings prepared from such compounds, oligomers, polymers, and blends thereof, processes for preparing such films and coatings, and electronic devices, especially electroluminescent devices comprised of one or more layers of such polymer films.

Polymers and oligomers of fluorenes substituted by alkyl groups at the 9-carbon position have been reported by Fukuda et al. in *Japanese Journal of Applied Physics*, Vol. 28, pp. L1433-L1435 (1989). Such polymers are disclosed as useful a luminescent materials in the preparation of light-emitting diodes. These polymers were prepared by the Kovacic procedure wherein the appropriate fluorene monomers were treated for several days with a large excess of oxidizing metal salts such as ferric chloride. The structures are represented as poly(fluorene-2,7'-diyl)s. A series of patents including U.S. Pat. Nos. 6,605,373, 6,362,310, 6,255,449, 6,255,447, 6,169,163, and 5,962,631 disclosed certain 2,7-disubstituted fluorene compounds further substituted at the 9 position with 1 or 2 substituents including $C_{1-20}$ hydrocarbyl groups or $C_{1-20}$ hydrocarbyl groups containing one or more S, N, O, P or Si atoms, $C_{4-16}$ hydrocarbyl carbonyloxy groups, $C_{4-16}$ aryl(trialkylsiloxy) groups, and alkylidenyl or divalent spirocycle forming groups such as 5-norborn-2-enylidenyl groups. Suitable substituents at the 2 and 7 positions included crosslinkable groups. An improved synthesis of such compounds was also disclosed in U.S. Pat. No. 5,777,070.

In JP 20-327640 certain 2-(diarylamino)-7-di(arylamino) aminofluorene derivatives were disclosed for use as hole transport materials in organic electroluminescent devices. Similar uses were disclosed for additional diarylaminofluorene derivatives in JP 09-258465. In JP 11-322679 the preparation of certain bisarylaminofluorenes was disclosed. In EP-A-823,669 a series of fluorene derivatives, including bis (diarylamino)fluorene compounds for use as photosensitive layer materials for organic light emitting diodes (OLEDs) were disclosed.

*Macromol. Rapid Commun.* 20, 224-228 (1999) and *Macromol. Rapid Commun.* 21, 583-589 (2000) describe certain crosslinkable triarylamine hole-transport materials suitable for use in preparation of multilayer organic light emitting devices by solution spin-coating techniques. *J. Phys. Org. Chem.* 16, 194-201 (2003), *Polymer Preprints* 43 (1), 104 (2002) and *Polymer Preprints* 44(1), 1061 (2003) elucidate the structure and electroluminescent properties of 9,9-didecyl-2,7-bis(N,N-diphenylamino)fluorene.

Recent advances in display technology have resulted in improved compounds and fabrication techniques for electroluminescent devices such as light-emitting diodes (LED's). High luminance materials are now available for a large portion of the visible light spectrum, including blue light emitting compounds. Recently it has been discovered that improved lifetimes and efficiencies of the active or light emitting layer of a multilayer LED can be obtained by incorporation of a charge transport layer into a multilayer LED between the active or light emitting layer and the anode. Such layers may also be referred to as a hole injection and/or hole transport layer where the purpose is to improve hole injection into the light emitting layer and to provide a buffer layer between the anode and the light emitting layer. In other applications, the inter-layer may act as an electron blocking layer to balance charge carriers for optimization of device efficiency and lifetime.

The present invention is directed to novel compounds for use in such interlayers of a multilayer LED, as well as in other electronic devices such as field effect transistors (FET's), photovoltaic cells, and even for integrated circuits or printed circuit boards.

SUMMARY OF THE INVENTION

According to the present invention there are provided compounds of the formula:

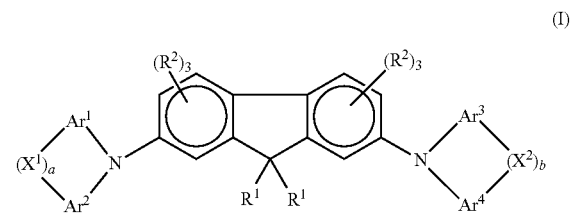

(I)

wherein $R^1$ is independently in each occurrence i) a $C_{1-40}$ hydrocarbyl group, ii) a $C_{1-40}$ hydrocarbyl group wherein one or more carbons are substituted by one or more heteroatoms selected from S, N, O, P, B or Si atoms, or iii) a halogenated derivative of i) or ii), with the proviso that, in at least one occurrence, $R^1$ is crosslinkable group;

$R^2$ is independently in each occurrence hydrogen, halogen, $C_{1-20}$ hydrocarbyl, $C_{1-20}$ hydrocarbyloxy, $C_{1-20}$ thioether, $C_{1-20}$ hydrocarbylcarbonyloxy, di($C_{1-20}$hydrocarbyl)amino, or cyano;

$Ar^1$, $Ar^2$, $Ar^3$ and $Ar^4$ are independently in each occurrence $C_{6-20}$ aromatic groups, optionally containing one or more S, N, O, P, B or Si heteroatoms, or a halo-, $C_{1-20}$ hydrocarbyl-, di($C_{1-20}$ hydrocarbyl)amino-, $C_{1-20}$ hydrocarbyloxy-, tri($C_{1-10}$ hydrocarbyl)silyl-, or tri($C_{1-10}$ hydrocarbyl)siloxy-substituted derivative thereof, a and b independently in each occurrence are 0 or 1; and $X^1$ and $X^2$ independently in each occurrence are O, S, $SO_2$, $CH_2$, $C(R^3)_2$ or $NR^3$, wherein $R^3$ is selected from the group consisting of $C_{1-22}$ alkyl, $C_{1-22}$ cycloalkyl, $C_{6-24}$ aryl, and $C_{7-24}$ aralkyl.

In a second aspect, this invention is a composition comprising oligomers or polymers having one or more repeating groups of the formula:

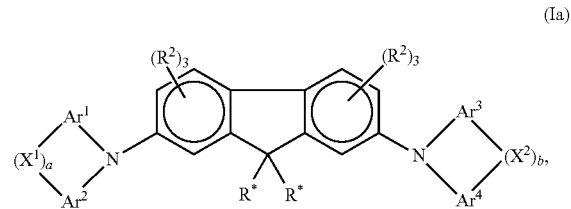

(Ia)

wherein R* is independently in each occurrence i) a $C_{1-40}$ hydrocarbyl group, ii) a $C_{1-40}$ hydrocarbyl group wherein one or more carbons are substituted by one or more heteroatoms selected from S, N, O, P, B or Si atoms, or iii) a halogenated derivative of i) or ii), with the proviso that in at least one occurrence, R* is a divalent linking group formed by crosslinking of a crosslinkable group selected from i), ii) or iii) through which the repeating groups are joined;

$R^2$ is independently in each occurrence hydrogen, halogen, $C_{1-20}$ hydrocarbyl, $C_{1-20}$ hydrocarbyloxy, $C_{1-20}$ thioether, $C_{1-20}$ hydrocarbylcarbonyloxy, di($C_{1-20}$hydrocarbyl)amino, or cyano;

$Ar^1$, $Ar^2$, $Ar^3$ and $Ar^4$ are independently in each occurrence $C_{6-20}$ aromatic groups, optionally containing one or more S, N, O, P, B or Si heteroatoms, halo-, $C_{1-20}$ hydrocarbyl-, di($C_{1-20}$ hydrocarbyl)amino-, $C_{1-20}$ hydrocarbyloxy-, tri($C_{1-10}$ hydrocarbyl)silyl-, or tri($C_{1-10}$ hydrocarbyl)siloxy-substituted derivatives thereof, or divalent derivatives of the foregoing;

a and b independently in each occurrence are 0 or 1; and $X^1$ and $X^2$ independently in each occurrence are a covalent bond, O, S, $SO_2$, $CH_2$, $C(R^3)_2$ or $NR^3$, wherein $R^3$ is selected from the group consisting of $C_{1-22}$ alkyl, $C_{1-22}$ cycloalkyl, $C_{6-24}$ aryl and $C_{7-24}$ aralkyl.

In a third aspect, this invention is a process for preparing oligomers or polymers comprising one or more bis(diarylamino)fluorene groups of formula (Ia), which comprises heating one or more compounds of formula (I) or a composition comprising the same, such as a mixture thereof with one or more additional polymerizable monomers, oligomers, or polymers, optionally in the presence of any other noninterfering compound, under reaction conditions sufficient to form an oligomer or polymer having one or more groups of Formula (Ia).

In a fourth aspect, this invention is a film comprising one or more of the oligomers or polymers of the second embodiment of this invention or preparable according to the third embodiment of this invention.

In a fifth aspect, this invention is an electronic device, especially an electroluminescent device such as a light emitting diode comprising one or more layers of polymer films, at least one of which comprises a film according to the fourth aspect of the invention.

The foregoing compounds, oligomers and polymers have been discovered to possess especially efficient hole injecting/transporting or electron blocking properties as interlayers in electronic devices, and advantageously are characterized by reduced ionization potential and improved conductivity. Moreover, the compounds are capable of forming crosslinked, solvent resistant films that are well suited for use as such interlayers in electronic devices such as LED's.

DETAILED DESCRIPTION OF THE INVENTION

For purposes of United States patent practice, the contents of any patent, patent application or publication referenced herein is hereby incorporated by reference in its entirety herein, especially with respect to its disclosure of monomer, oligomer or polymer structures, synthetic techniques and general knowledge in the art. If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise or apparent from the context, refers to the listed members individually as well as in any combination.

As used herein the term "aromatic" refers to a polyatomic, cyclic, ring system containing (4δ+2) π-electrons, wherein δ is an integer greater than or equal to 1. The term "fused" as used herein with respect to a ring system containing two or more polyatomic, cyclic rings means that with respect to at least two rings thereof, at least one pair of adjacent atoms is included in both rings.

"B-Staged" refers to the oligomeric mixture or low molecular weight polymeric mixture resulting from partial polymerization of a monomer. Unreacted monomer may be included in the mixture.

"Crosslinkable" refers to a functional group that is capable of being irreversibly cured or polymerized, generally upon heating, thereby forming a material that cannot be reshaped or reformed. Crosslinking may be assisted by UV, microwave, x-ray, or e-beam irradiation and assisted by use of a catalyst or initiator. The term is often used interchangeably with "thermosettable" when the crosslinking is done thermally.

"Inert substituent" means a substituent group which does not interfere with any subsequent desirable polymerization reaction of the monomer or B-staged oligomer and does not include further polymerizable ring structures as disclosed herein.

Preferred substituents, $R^1$, are selected from $C_{1-40}$ hydrocarbyl, $C_{3-40}$ hydrocarbyl containing one or more S, N, O, P, or Si heteroatoms, and the foregoing $C_{1-40}$ hydrocarbyl, $C_{3-40}$ heteroatom containing groups containing a crosslinkable group. Preferred crosslinkable groups contain an unsaturated bond, either a double bone, a triple bond, a precursor capable of in situ formation of a double bond, or a heterocyclic, addition polymerizable group. Most preferred crosslinkable $R^1$ groups contain a polymerizable vinyl group or precursor thereof. Examples of suitable crosslinkable $R^1$ groups include:

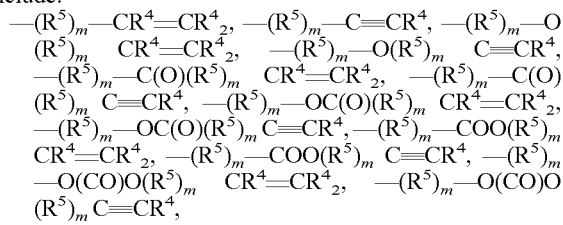

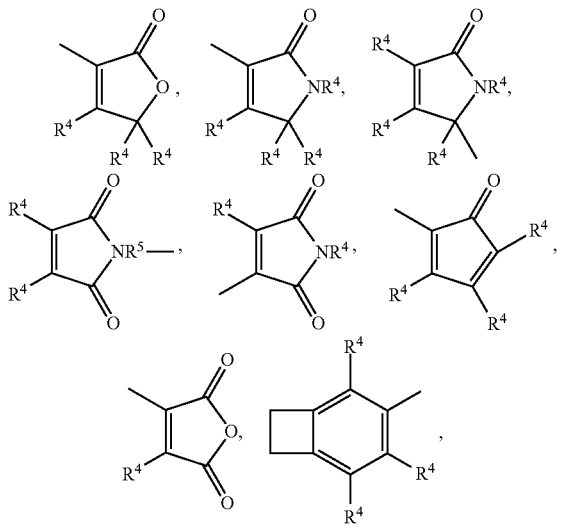

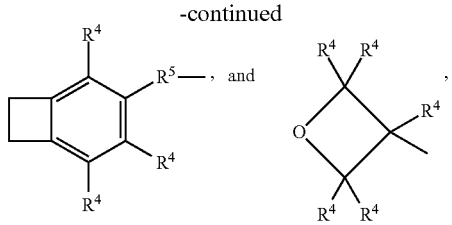

where
R⁴ is hydrogen, halogen, $C_{1-20}$ hydrocarbyl, $C_{1-20}$ halohydrocarbyl, or $C_{1-20}$ halocarbyl;
R⁵ is $C_{1-20}$ hydrocarbylene, $C_{1-20}$ halohydrocarbylene, or $C_{1-20}$ halocarbylene; and
m is 0 or 1.

Preferred R¹ groups are vinyl, $C_{1-4}$ alkylacrylate, vinylphenyl, vinylphenyloxy, maleimido, vinylbenzyl, vinylbenzyloxy, oxetanyl, 2-propynyl, trifluoroethenyl, 1-benzo-3,4-cyclobutane, and methyl-1-benzo-3,4-cyclobutane.

Preferred R² groups are hydrogen, $C_{1-20}$ hydrocarbyl, $C_{1-20}$ halohydrocarbyl, $C_{1-20}$ halocarbyl, $C_{1-20}$ hydrocarbyloxy, $C_{1-20}$ hydrocarbylthio, $C_{1-20}$ hydrocarbonyloxy, $C_{1-20}$ hydrocarbyloxycarbonyl, $C_{1-20}$ hydrocarbylcarbonyloxy, or cyano, most preferably hydrogen.

Preferred groups Ar¹, Ar², Ar³ and Ar⁴ are phenyl or phenylene, preferred X¹ and X² groups are O or S, and preferably a and b are 0 or 1.

The uncrosslinked compounds of the invention may be prepared by reacting a 2,7-dihalofluorene compound able to react at the 9 position, such as 2,7-dihalo-9-fluorenone, with a precursor able to form the desired R¹ functional group. Diarylamino functionality is then incorporated in the 2 and 7 positions using conventional synthetic, routes.

Oligomeric homopolymers and crosslinked homopolymers consisting essentially of groups of Formula (Ia) are readily prepared upon heating and curing of the monomers of formula 1). B-staging of the monomer can be employed to produce a composition having improved flow and self-leveling properties, however the present monomers are of sufficiently low viscosity that B-staging is not required prior to use in forming films. The monomers can also be employed in the formation of copolymers in order to impart partially crosslinking and improved solvent resistance to the resulting polymer. Desirably, such copolymers comprise from 1 to 50 mole percent of the groups of Formula (Ia), more preferably from 2 to 30 mole percent, and most preferably from 5 to 20 mole percent.

Suitable reactive comonomers that may be copolymerized with the compounds of formula (I) are compounds including a reactive group capable of undergoing chain extension or crosslinking with a crosslinkable R¹ group to form an oligomer or polymer. Examples include compounds containing a glycidyl ether, acrylate ester, methacrylate ester, ethenyl, ethynyl, maleimide, or cyclobutene moiety. Preferred examples are p-divinyl benzene and 1,5-divinylnaphthalene.

The fluorene oligomers or polymers of the invention demonstrate strong photo-luminescence in dilute solutions or in the solid state. When such materials are exposed to a light of a wavelength of 300 to 700 nanometers, the materials emit light of wavelengths in the region of 400 to 800 nanometers. More preferably, such materials absorb light of wavelengths of from 350 to 400 nanometers and emit light of wavelengths in the region of 400 to 650 nanometers. The uncrosslinked fluorene of the invention are readily soluble in common organic solvents. They are processable into thin films or coatings by conventional techniques such as solution spin coating, lithography, or ink-jet printing using solvents such as toluene, xylene, mesitylene or ethylbenzene.

The fluorene oligomers or B-staged polymers of this invention preferably have a weight average molecular weight 500 to 5000 Daltons as determined by gel permeation chromatography using polystyrene standards. The compounds and oligomers can be used as one component of a blend or mixture of crosslinkable compounds as well. Desirably, the present compounds or oligomers comprise from 1 to 50 percent of the crosslinkable composition, more preferably from 5 to 25 percent.

The compounds of the invention are desirably crosslinked to form solvent resistant, heat-resistant films at temperatures of 100° C. or more, more preferably at 150° C. or more. Preferably, such crosslinking occurs at 350° C. or less, more preferably 300° C. or less and most preferably 250° C. or less. The crosslinkable compounds, oligomers and polymers of the invention are stable at 60° C. or more and more preferably 150° C. or more. "Stable" as used herein means that such oligomers do not undergo crosslinking or polymerization reactions at or below the stated temperatures. Additives such as catalysts or free radical initiators can be included in the crosslinkable composition to assist in forming cured polymers according to the invention. Suitable additives include peroxides such as benzoyl peroxide, or other free radical generating compound.

The primary use for the oligomers and polymers of the invention is in the formation of films. Such films can be used as fluorescent or phosphorescent coatings in general and as interlayers, protective coatings, and hole transport and electron blocking layers in electronic devices such as polymeric light emitting diodes. The thickness of the coating or film is dependent upon the ultimate use. Generally, such thickness can be from 0.01 to 200 micrometers. When used as a coating, the film thickness is desirably from 50 to 200 micrometers. When used as protective layers, the film thickness is desirably from 5 to 20 micrometers. When used as a charge transport layer in a polymeric light emitting diode, the film thickness is desirably from 0.05 to 2 micrometers. The oligomers or polymers of the invention form films that are substantially lacking in pinholes and other defects. Such films can be prepared by means well known in the art including spin-coating, spray-coating, dip-coating, roller-coating and ink jet printing. Such coatings are prepared by a process wherein a composition comprising the present compounds, oligomers or polymers is applied to a substrate and exposed to conditions such that a film is formed. The conditions which form a film depend upon the application technique and the reactive end groups of the film forming moieties. Preferably, the solution contains from 0.1 to 10 weight percent of the oligomers or polymers of the invention, and the remainder solvent and/or other polymer forming components. For thin coatings, it is preferred that the composition contains from 0.5 to 5.0 percent by weight of the compounds, oligomers or polymers. This composition is then applied to the appropriate substrate by the desired method and the solvent is allowed to evaporate. Residual solvent may be removed by vacuum and/or by heat If the solvent is low boiling, then low solution concentrations, for example, 0.1 to 2 percent, are desired. If the solvent is high boiling, then high concentrations, for example, 3 to 10 percent, are desired. After removal of the solvent, the coating is then exposed to the necessary conditions to cure the film, if needed, to prepare a film having high solvent and heat resistance. The films are preferably substantially uniform in thickness and substantially free of pinholes. Preferably, the films are cured when exposed to temperatures of 80° C. or greater, more preferably 100° C. or greater, and most preferably 150° C. or greater. Preferably, the films cure at a temperature of 300° C. or less.

In the preparation of the films, the composition may further comprise a catalyst suitable to facilitate or initiate the curing of the films. Such catalysts are well known in the art, for instance, for materials having ethylenic unsaturation, a free radical catalyst may be used. For aryl moieties with glycidyl ethers as end-groups, ureas or imidazoles may be used. In the preparation of films from fluorenes with glycidyl ether aryl-terminal moieties, such materials may be reacted with commonly known curing agents which facilitate crosslinking. Among preferred curing agents are tetrahydrophthalic anhydride, methylbicyclo[2.2.1]heptane-2,3-dicarboxylic anhydride (nadic anhydride), and maleic anhydride.

In another desirable embodiment, the monomers and oligomers may be partially cured or B-staged prior to forming the film. In such embodiment, the composition is exposed to conditions such that only a portion of the reactive materials cure or crosslink. This is commonly used to improve the processability of composition and can facilitate the preparation of films. Such B-staged material can thereafter be used to prepare coatings by the means disclosed above. Preferably, 10 percent or greater of the reactive moieties are reacted during B-staging. Preferably, 50 percent or less of the reactive moieties are reacted.

Yet another aspect of the invention relates to electronic devices including as one component a film comprising the polymers of this invention. Electronic devices, especially LED's typically consist of an organic film sandwiched between an anode and a cathode such that when a positive bias is applied to the device, holes are injected into the organic film from the anode, and electrons are injected from the cathode. The combination of a hole and an electron may give rise to an exciton which undergoes radiative decay to the ground state by liberating a photon. In practice the anode is commonly a mixed oxide of tin and indium for its conductivity and transparency. The mixed oxide (normally indium tin dioxide or ITO) is deposited on a transparent substrate such as glass or plastic so that the light emitted by the organic film may be observed. The organic film may be the composite of several individual layers each designed for a distinct function. Since holes are injected from the anode, the layer next to the anode needs to have the functionality of transporting holes. Similarly, the layer next to the cathode needs to have the functionality of transporting electrons. In many instances, the hole- or electron-transporting layers also act as the light emitting layer. In other instances, the functions of hole and/or electron transport and light emission are performed by different layers. The individual layers of the organic film may be all polymeric in nature or combinations of films of polymers and films of small molecules formed by vapor deposition. It is preferred that the total thickness of the organic film be less than 1000 nm, more preferably less than 500 nm, most preferably less than 300 nm. One embodiment of the instant invention is electronic devices whose organic film comprises at least one of the polymeric compositions of this invention.

The ITO-glass which serves as the substrate and the anode may be used for coating after the usual cleaning with detergent, organic solvents and UV-ozone treatment. It may also be first coated with a thin layer of a conducting substance to facilitate hole injection, surface leveling, and/or film adhesion. Such substances include copper phthalocyanine, polyaniline and poly(3,4-ethylenedioxythiophene) (PEDT); the last two of which are rendered conductive by doping with a strong organic acid, e.g., poly(styrenesulfonic acid). It is preferred that the thickness of this layer be 200 nm or less; more preferably 100 nm or less.

The present compounds may be used in the preparation of interlayers in a multilayer device or as one component of a mixture of compounds forming a hole transporting polymer layer or as a separate hole transporting layer in a multilayer electroluminescent device. In the case where a hole-transporting polymer other than the present invention is used, known hole-conducting polymers, such as polyvinylcarbazole, or the polymeric aryl amines disclosed in U.S. Pat. Nos. 6,605,373, 6,362,310, 6,255,449, 6,255,447, 6,169,163, 5,962,631, 5,929,194 or 5,728,801 may be employed. The resistance of this layer to erosion by the solution of the copolymer film which is to be applied next is obviously critical to the successful fabrication of multi-layer devices. Accordingly the copolymers of this invention are normally applied from solutions such as xylene or toluene in which any previously deposited layer is insoluble. By either forming a crosslinked film of the present polymers as a hole-transporting or electron blocking layer or by covering or protecting a previously deposited hole-transporting or electron blocking layer with an interlayer comprising a crosslinked polymer according to the present invention, the assembly can be protected from subsequent reagents or solvents employed in manufacture of the LED. The thickness of the hole-transporting layer, electron blocking, or interlayer according to the invention is desirably 500 nm or less, preferably 300 nm or less, most preferably 150 nm or less.

Low molecular weight or small molecule materials usefully employed as hole transport layers in the electronic devices of the present invention include the metal complexes of 8-hydroxyquinoline (as described by Burrows et al. in *Applied Physics Letters*, Vol. 64, pp. 2718-2720 (1994)), metallic complexes of 10-hydroxybenzo(h)quinoline (as described by Hamada et al. in *Chemistry Letters, pp.* 906-906 (1993)), 1,3,4-oxadiazoles (as described by Hamada et al. in *Optoelectronics—Devices and Technologies*, Vol. 7, pp. 83-93 (1992)), 1,3,4-triazoles (as described by Kido et al. in *Chemistry Letters*, pp. 47-48 (1996)), and dicarboximides of perylene (as described by Yoshida et al. in *Applied Physics Letters*, Vol. 69, pp. 734-736 (1996)).

Polymeric electron-transporting (light emitting) materials for use in LED's according to the present invention are exemplified by oxadiazole-containing polymers (as described by Li et al. in *Journal of Chemical Society*, pp. 2211-2212 (1995), by Yang and Pei in *Journal of Applied Physics*. Vol 77, pp. 4807-4809 (1995) and EP-A-875,947), 1,3,4-triazole-containing polymers (as described by Strukelj et al. in *Science*. Vol. 267, pp. 1969-1972 (1995)), quinoxaline-containing polymers (as described by Yamamoto et al. in *Japan Journal of Applied Physics*. Vol. 33, pp. L250-L253 (1994), O'Brien et al. in *Synthetic Metals*. Vol. 76, pp. 105-108 (1996)), and cyano-PPV (as described by Weaver et al. in *Thin Solid Films* Vol. 273, pp. 39-47 (1996)). The thickness of this layer may be 500 nm or less, preferably 300 nm or less, most preferably 150 nm or less.

The metallic cathode may be deposited either by thermal evaporation or by sputtering. The thickness of the cathode may be from 100 nm to 10,000 nm. The preferred metals are calcium, magnesium, indium, and aluminum. Alloys of these metals may also be used. Alloys of aluminum containing 1 to 5 percent of lithium and alloys of magnesium containing at least 80 percent of magnesium are preferred.

The electroluminescent devices of this invention emit light when subjected to an applied voltage of 50 volts or less with luminance efficiency as high as 3.5 Cd/A.

In a preferred embodiment, the electroluminescent device comprises at least one hole-transporting polymer film comprised of a polymer of the invention and a light-emitting polymer film arranged between an anode material and a cathode material such that under an applied voltage holes are injected from the anode material into the hole-transporting polymer film and electrons are injected from the cathode material into the light-emitting polymer film when the device is forward biased, resulting in light emission from the light-emitting layer. In another preferred embodiment, multiple layers each comprising one or more hole-transporting polymers are arranged so that the layer closest to the anode has the lower oxidation potential, with the adjacent layers having progressively higher oxidation potentials. By these methods, electroluminescent devices having relatively high light output per unit voltage and a broad spectrum of output, including white light, may be prepared.

The term "hole-transporting polymer film" as used herein refers to a layer of a film of a polymer which when disposed between two electrodes to which a field is applied and holes are injected from the anode, permits adequate transport of holes into the emitting polymer. Hole-transporting polymers typically are comprised of triarylamine moieties. Additives or "dopants" such as tris(4-bromophenyl)aminium hexachloroantimonate may be added to the polymer to modify hole transport properties of the polymer. The term "light-emitting polymer film" as used herein refers to a layer of a film of a polymer whose excited states can relax to the ground state by emitting photons, preferably corresponding to wavelengths in the visible range. The term "anode material" as used herein refers to a semi-transparent, or transparent, conducting film with a work function between 4.5 electron volts (eV) and 5.5 eV. Examples are oxides and mixed oxides of indium and tin, and gold. The term "cathode material" as used herein refers to a conducting film with a work function between 2.5 eV and 4.5 eV. Examples are lithium, calcium, magnesium, indium, silver, aluminum, or blends and alloys of the above.

It is expressly intended that the foregoing disclosure of preferred or desired, more preferred or more desired, highly preferred or highly desired, or most preferred or most desired substituents, ranges, end uses, processes, or combinations with respect to any one of the embodiments of the invention is applicable as well to any other of the preceding or succeeding embodiments of the invention, independently of the identity of any other specific substituent, range, use, process, or combination.

The following examples are included for illustrative purposes only and do not limit the scope of the claims. Unless otherwise stated, implicit from the context or conventional in the art, all parts and percentages are by weight. It is understood that the present invention is operable in the absence of any component which has not been specifically disclosed. The term "overnight", if used, refers to a time of approximately 16-18 hours, "room temperature", if used, refers to a temperature of about 20-25° C.

Example 1

Preparation of 9,9-di(4-(4-vinylphenyl)methoxyphenyl)-2,7-bis(diphenylamino)fluorene (4)

The title compound was prepared using the following synthetic route:

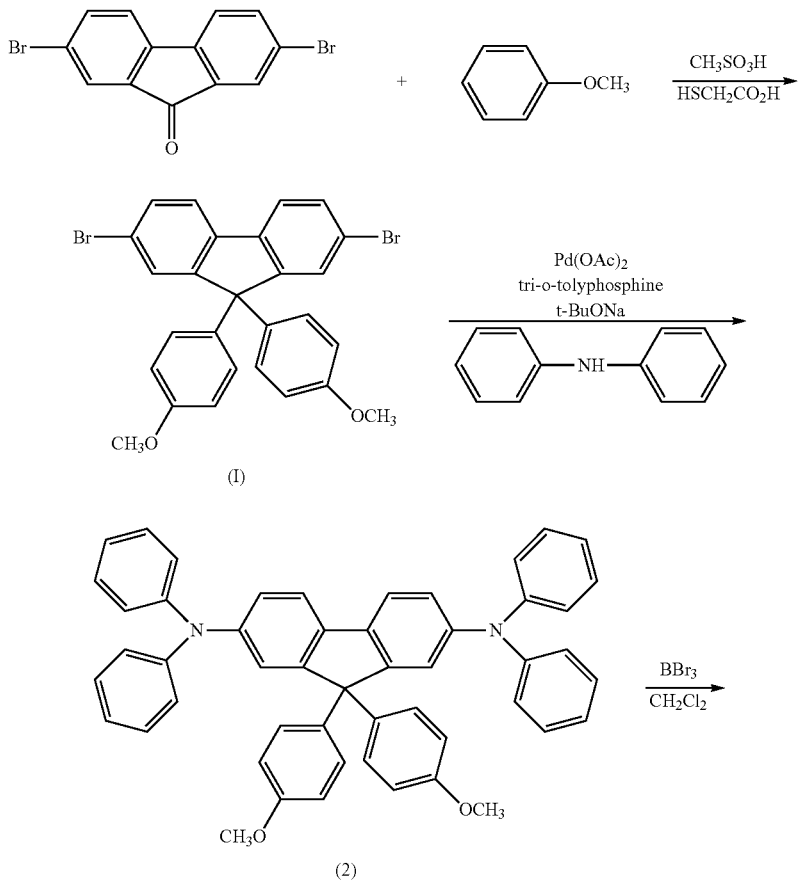

-continued

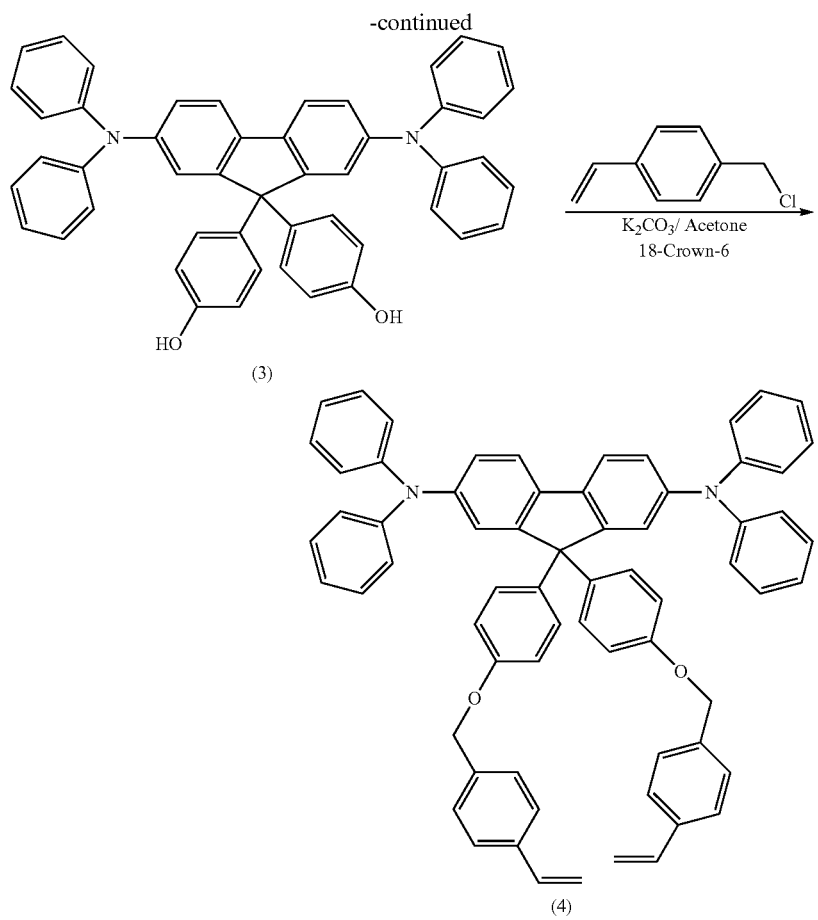

Compound 1: A mixture of dibromofluorenone (9 g, 26.6 mmol), anisole (25 ml), methanesulfonic acid (20 ml), and mercaptoacetic acid (0.5 ml) is stirred under nitrogen at room temperature overnight HPLC indicates the complete conversion of dibromofluorenone. Next, 50 ml of methanol is added slowly into the reaction mixture. The light orange precipitates are collected by filtration and washed with methanol. Drying under reduce pressure at 50° C. overnight affords 2,7-dibromo-9,9-di(4-methoxyphenyl)fluorene (Compound 1) as a yellow powder (12.1 g).

Compound (2): 0.18 g (0.8 mmol) of palladium acetate and 0.49 g (1.6 mmol) of tri-o-tolylphosphine are dissolved in 25 ml of toluene and the solution stirred at room temperature for 10 min. To the solution, 6.0 g (11.2 mmol) of 2,7-dibromo-9,9-di(4-methoxyphenyl)fluorene (Compound 1), 5.68 g (33.6 mmol) of diphenylamine, and 3.84 g (40 mmol) of potassium tert-butoxide are added. The mixture is refluxed under nitrogen overnight. After being cooled to room temperature, 1 N HCl is added slowly until the pH value reached 5-6. The solution is passed through a neutral alumina column eluted with toluene. After being concentrated, the toluene solution is poured into 300 ml of methanol to precipitate the product. The precipitate is recrystallized from toluene to give 5.5 g of the title compound as a yellow powder.

Compound (3): 5.36 g (7.52 mmol) of 9,9-di(4-methoxyphenyl)-2,7-bis(diphenylamino)fluorene (Compound 2) is dissolved in 25 ml of dichloromethane and the solution cooled in a dry ice-acetone bath under the protection of flowing nitrogen. To this solution, 34 ml (34 mmol) of a 1.0 M solution of boron tribromide in dichloromethane is added dropwise while the reaction is stirred. After the addition of boron tribromide, the reaction mixture is allowed to warm to room temperature and is stirred at room temperature overnight. The reaction mixture is then poured into 300 g of crushed ice. Concentrated HCl (1.0 ml) is added and the aqueous mixture stirred at room temperature for 2 h. The mixture is then extracted with dichloromethane and the combined organic layer is dried over anhydrous magnesium sulfate. The solution is filtered and the solvent removed on a rotary evaporator. The crude product is re-dissolved in a small amount of ethyl acetate and purified on a silica gel column eluted by a mixture of ethyl acetate and hexane (9:1 v/v). After the solvent is removed, the solid is re-crystallized from the mixed solvent of ethanol and ethyl acetate to give 3.5 g of the final product as off-white crystals. Purity: 96.7 percent (HPLC)

Compound (4): 3.1 g (4.53 mmol) of Compound (3) and 3.45 g (22.6 mmol) of 4-vinylbenzyl chloride are dissolved in 50 ml of anhydrous acetone. Anhydrous potassium carbonate (4.14 g, 30 mmol) and 0.2 g of 18-crown-6 are added to the solution. The reaction is refluxed under nitrogen overnight. The mixture is then cooled to room temperature and 200 ml of THF are added before the solution is filtered. The filtrate is concentrated to 10 ml and poured into 200 ml of methanol. The product precipitates as a white powder. The crude product is then re-dissolved in a small amount of toluene and purified twice on a silica gel column eluted with a mixture of toluene and hexane (9:1 v/v). After being dried under reduced pressure at room temperature for 24 h, 3.2 g of a white powder is obtained. HPLC analysis discloses two components, one major and one minor, in the final product. The major product has an area percent assay of 963±0.3 percent at 280 nm and 95.8±0.2 percent at 320 nm. The minor product has an area percent assay of 3.2±0.3 percent at 280 nm and 3.7±0.2 percent at 320 nm. Analysis by APCI/LC/MS (atmospheric pressure chemical ionization liquid chromatography mass spectrometry) identifies the major content as the title compound or isomer (Mw 916) and the minor-content is tentatively identified as the monobromide of the title compound (Mw 994).

Example 2

Preparation of Crosslinked Film

A 5 percent solution of 9,9-di(4-(4-vinylphenyl)methoxyphenyl)-2,7-bis(diphenylamino)-fluorene in mixed xylenes is spin-coated on a glass substrate at 2000 rpm. A good quality film is obtained having a thickness of about 50 nm. The film is heated on a hotplate at 180° C. for 30 min. After baking in the foregoing manner, the film is insoluble in mixed xylenes. The annealed film emits blue light under an UV lamp.

Example 3

Light Emitting Devices Using Doped 9,9-di(4-(4-vinylphenyl)methoxyphenyl)-2,7-bis(diphenylamino)fluorene Film as Hole-Transporting Layer Material 240 mg of 9,9-di(4-(4-vinylphenyl)methoxyphenyl)-2,7-bis(diphenylamino)fluorene and 24 mg of tris(4-bromophenyl)aminium hexachloroantimonate (TBPAH, available from Sigma-Aldrich, Inc.) are dissolved in 4 ml of mixed xylenes. The solution is shaken at room temperature overnight and then filtered through a 0.45 µm nylon syringe filter. On a cleaned ITO-coated glass substrate, a 9,9-di(4-(4-vinylphenyl)methoxyphenyl)-2,7-bis(diphenylamino)fluorene film of about 80 nm thickness is deposited by spin-coating the solution at 4000 rpm. The film is then heated in a nitrogen-filled oven at 180° C. for 30 min to create an insoluble hole-transporting layer. On the top of the hole-transporting layer, an electron transporting polymer layer (LUMATION™ Green 1300 Series, available from The Dow Chemical Company (80 nm)) is spin-coated from a solution in xylenes (1.3 g/100 ml). The cathode metals (Ca, 10 nm and Al, 150 nm) are vapor deposited over the polymer film. The device emits yellowish green light upon applying a dc voltage, having a brightness of 200 cd/m² at 7.5 V with light efficiency of 1.1 cd/A. At about 9.0 V, the brightness reaches 1000 cd/m² with the light efficiency of about 2 cd/A. The maximum efficiency was measured as about 3 cd/A, reached at 12 V with a brightness of 4000 cd/m², and maximum brightness was about 13,000 cd/m².

Example 4

Light Emitting Devices Using Blends of Doped 9,9-di(4-(4-vinylphenyl)methoxyphenyl)-2,7-bis(diphenylamino)fluorene and poly(9,9-dioctylfluorene-co-bis-N,N'-(4-butylphenyl)-bis-N,N'-phenyl-1,4-phenylenediamine) (PFB) as the Hole-Transporting Film Materials PFB (80 mg, disclosed in U.S. Pat. No. 6,605,373) and having the following repeat structure:

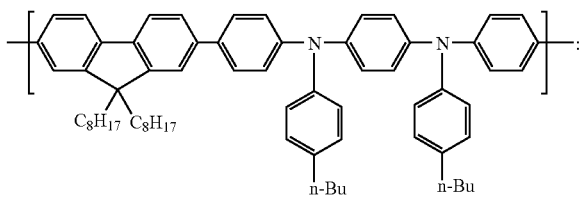

and 16 mg of 9,9-di(4-(4-vinylphenyl)methoxyphenyl)-2,7-bis(diphenylamino)fluorene are dissolved in 4 ml of xylenes. The solution is shaken at room temperature overnight and filtered through a 0.45 µm nylon syringe filter. On a cleaned ITO-coated glass substrate, a polymer film of about 80 nm thickness is spin-coated from the solution. The film is then heated in a nitrogen-filled oven at 180° C. for 30 min to create a solvent-resistant hole-transporting layer. On the top of the hole-transporting layer, an electron transporting polymer layer of LUMATION™ Green 1300 Series (available from The Dow Chemical Company) about 80 nm in thickness is spin-coated from a solution in xylenes (1.3 g/100 ml). The cathode metals (Ca, 10 nm and Al, 150 nm) are vapor deposited over the polymer film. The devices shows a maximum brightness of about 15,000 cd/m² and maximum efficiency of 3 cd/A (at about 10,000 cd/m²). The efficiency at 200 cd/m² is 1.3 cd/A (at 9.5 V).

Example 5

Light Emitting Devices Using Doped Blends of 9,9-di(4-(4-vinylphenyl)methoxyphenyl)-2,7-bis(diphenylamino)fluorene and PFB as the Hole-Transporting Film Materials PFB (80 mg), 16 mg of 9,9-di(4-(4-vinylphenyl)methoxyphenyl)-2,7-bis(diphenylamino)fluorene, and 9.6 mg of TBPAH are dissolved in 4 ml of mixed xylenes. The solution is shaken at room temperature overnight and filtered through a 0.45 µm nylon syringe filter. On a cleaned ITO coated glass substrate, a polymer film approximately 80 nm thick is spin-coated from the solution. The film is then heated in a nitrogen-filled oven at 180° C. for 30 min to create a solvent-resistant hole-transporting layer. On the top of the hole-transporting layer, an electron transporting polymer layer of LUMATION™ Green 1300 Series (available from The Dow Chemical Company) 80 nm thickness is spin-coated from a solution in xylenes (1.3 g/100 ml). The cathode metals (Ca, 10 nm and Al, 150 nm) are vapor deposited over the polymer film. The device shows the maximum brightness of about 14,500 cd/m² and a maximum efficiency of 3 cd/A (at about 10,000 cd/m²). The efficiency at 200 cd/m² is 1.5 cd/A (at about 7.0 V).

The invention claimed is:
1. A compound of the formula:

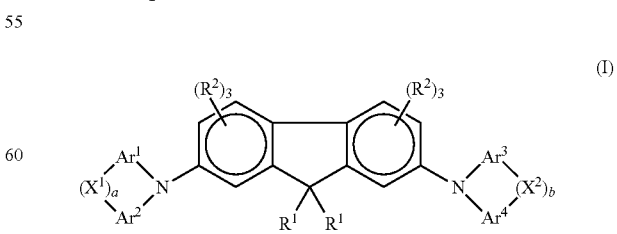

wherein $R^1$ is independently in each occurrence i) a $C_{1-40}$ hydrocarbyl group, ii) a $C_{1-40}$ hydrocarbyl group wherein one or more carbons are substituted by one or more heteroatoms selected from S, N, O, P, B or Si atoms, or iii) a halogenated derivative of i) or ii), with the proviso that in at least one occurrence, $R^1$ is crosslinkable group, and wherein $R^1$ in at least one occurrence is selected from the group consisting of
$-(R^5)_m-CR^4=CR^4_2$, $-(R^5)_m-CR^4=CR^4$, $-(R^5)_m-O(R^5)_m CR^4=CR^4_2$, $-(R^5)_m-O(R^5)_m C=CR^4$, $-(R^5)_m-C(O)(R^5)_m CR^4=CR^4_2$, $-(R^5)_m-C(O)(R^5)_m C=CR^4$, $-(R^5)_m-OC(O)(R^5)_m C=CR^4$, $-(R^5)_m-COO(R^5)_m CR^4=CR^4_2$, $-(R^5)_m-COO(R^5)_m C=CR^4$, $-(R^5)_m O(CO)O(R^5)_m CR^4=CR^4_2$, $-(R^5)_m-O(CO)O(R^5)_m C=CR^4$,

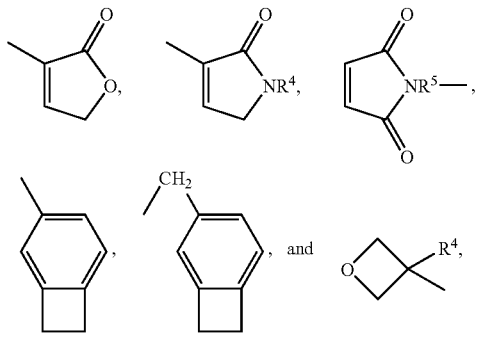

where $R^4$ is hydrogen, halogen, $C_{1-20}$ hydrocarbyl, $C_{1-20}$ halohydrocarbyl, or $C_{1-20}$ halocarbyl; $R^5$ is $C_{1-20}$ hydrocarbylene, $C_{1-20}$ halohydrocarbylene, or $C_{1-20}$ halocarbylene; and m is 0 or 1;

$R^2$ is independently in each occurrence hydrogen, halogen, $C_{1-20}$ hydrocarbyl, $C_{1-20}$ hydrocarbyloxy, $C_{1-20}$ thioether, $C_{1-20}$ hydrocarbylcarbonyloxy, di($C_{1-20}$hydrocarbyl)amino, or cyano;

$Ar^1$, $Ar^{21}$, $Ar^3$ and $Ar^4$ are independently in each occurrence $C_{6-20}$ aromatic groups, optionally containing one or more S, N, O, P, B or Si heteroatoms, or a halo-, $C_{1-20}$ hydrocarbyl-, di($C_{1-20}$hydrocarbyl)amino-, $C_{1-20}$hydrocarbyloxy-, tri($C_{1-10}$hydrocarbyl)silyl-, or tri($C_{1-10}$ hydrocarbyl)siloxy-substituted derivative thereof;

a and b independently in each occurrence are 0 or 1; and $X^1$ and $X^2$ independently in each occurrence are a covalent bond, O, S, $SO_2$, $CH_2$, $C(R^3)_2$ or $NR^3$, wherein $R^3$ is selected from the group consisting of $C_{1-22}$ alkyl, $C_{1-22}$ cycloalkyl, $C_{6-24}$ aryl, and $C_{7-24}$ aralkyl.

2. A compound according to claim 1 wherein $R^1$ independently each occurrence is selected from the group consisting of $C_{1-40}$ hydrocarbyl, $C_{3-40}$ hydrocarbyl containing one or more S, N, O, P, or Si heteroatoms, and the foregoing $C_{1-40}$ hydrocarbyl or $C_{3-40}$ heteroatom containing groups containing a crosslinkable group, with the proviso that in at least one occurrence, $R^1$ comprises crosslinkable group.

3. A compound according to claim 1 wherein $R^1$ in at least one occurrence contains a double bond, a triple bond, a precursor capable of in situ formation of a double bond, or a heterocyclic, addition polymerizable group.

4. A compound according to claim 1 wherein $R^1$ is selected from the group consisting of vinyl, vinylphenyl, vinylphenyloxy, maleimido, vinylbenzyl, vinylbenzyloxy, oxetanyl, 2-propynyl, trifluoroethenyl, 1-benzo-3,4-cyclobutane, and methyl-1-benzo-3,4-cyclobutane.

5. A compound according to claim 1 wherein $R^2$ independently each occurrence is hydrogen, $C_{1-20}$ hydrocarbyl, $C_{1-20}$ halohydrocarbyl, $C_{1-20}$ halocarbyl, $C_{1-20}$ hydrocarbyloxy, $C_{1-20}$ hydrocarbylthio, $C_{1-20}$ hydrocarbonyloxy, $C_{1-20}$ hydrocarbyloxycarbonyl, $C_{1-20}$ hydrocarbyl-carbonyloxy, or cyano.

6. A compound according to claim 5 wherein $R^2$ each occurrence is hydrogen.

7. A compound according to claim 1 wherein $Ar^1$, $Ar^2$, $Ar^3$ and $Ar^4$ are phenyl or phenylene, $X^1$ and $X^2$ are O or S, and a and b are 0 or 1.

8. An oligomer or polymer having one or more repeating groups of the formula:

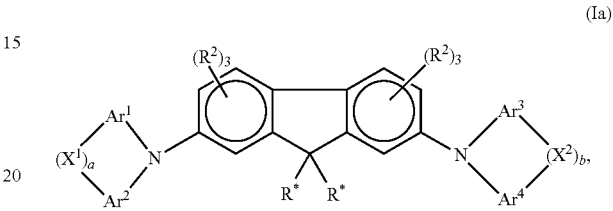

(Ia)

wherein $R^*$ is independently in each occurrence i) a $C_{1-40}$ hydrocarbyl group, iii) a $C_{1-40}$ hydrocarbyl group wherein one or more carbons are substituted by one or more heteroatoms selected from S, N, O, P, B or Si atoms, or iii) a halogenated derivative of i) or ii), with the proviso that in at least one occurrence, $R^1$ is a divalent linking group formed by crosslinking of a crosslinkable group selected from i), ii) or iii) through which the repeating groups are joined;

$R^2$ is independently in each occurrence hydrogen, halogen, $C_{1-20}$ hydrocarbyl, $C_{1-20}$ hydrocarbyloxy, $C_{1-20}$ thioether, $C_{1-20}$ hydrocarbylcarbonyloxy, di($C_{1-20}$hydrocarbylamino, or cyano;

$Ar^1$, $Ar^2$, $Ar^3$ and $Ar^4$ are independently in each occurrence $C_{6-20}$ aromatic groups, optionally containing one or more S, N, O, P, B or Si heteroatoms, halo-, $C_{1-20}$ hydrocarbyl-, di($C_{1-20}$ hydrocarbylamino-, $C_{1-20}$ hydrocarbyloxy-, tri($C_{1-10}$ hydrocarbyl)silyl-, or tri(Cmo hydrocarbylsiloxy-substituted derivatives thereof, or divalent derivatives of the foregoing;

a and b independently in each occurrence are 0 or 1; and $X^1$ and $X^2$ independently in each occurrence are a covalent bond, O, S, $SO_2$, $CH_2$, $C(R^3)_2$ or $NR^3$, wherein $R^3$ is selected from the group consisting of $C_{1-22}$ alkyl, $C_{1-22}$ cycloalkyl, $C_{6-24}$ aryl, and $C_{7-24}$ aralkyl.

9. A composition comprising an oligomer or polymer according to claim 8.

10. A process for preparing oligomers or polymers comprising heating a composition according to claim 1 under reaction conditions sufficient to form an oligomer or polymer having one or more groups according to claim 8.

11. A composition according to claim 8 in the form of a film.

12. An electronic device comprising one or more layers of polymer films, at least one of which comprises a film according to claim 11.

13. An electronic device according to claim 12 which is an electroluminescent device.

14. A compound according to claim 1, wherein a and b are 1.

* * * * *